US011974923B1

(12) United States Patent
Cassuto et al.

(10) Patent No.: US 11,974,923 B1
(45) Date of Patent: May 7, 2024

(54) PENILE PROSTHESIS IMPLANTATION SYSTEM

(71) Applicants: James Cassuto, Amarillo, TX (US); Mark Ferretti, Kingston, PA (US)

(72) Inventors: James Cassuto, Amarillo, TX (US); Mark Ferretti, Kingston, PA (US)

( * ) Notice: Subject to any disclaimer, the term of this patent is extended or adjusted under 35 U.S.C. 154(b) by 132 days.

(21) Appl. No.: 17/532,006

(22) Filed: Nov. 22, 2021

Related U.S. Application Data

(60) Provisional application No. 63/152,123, filed on Feb. 22, 2021.

(51) Int. Cl.
*A61F 2/26* (2006.01)
*A61F 5/41* (2006.01)

(52) U.S. Cl.
CPC ............ *A61F 2/26* (2013.01); *A61F 2005/411* (2013.01); *A61F 2250/0003* (2013.01)

(58) Field of Classification Search
CPC .............................. A61F 2/26; A61F 2005/411
See application file for complete search history.

(56) References Cited

U.S. PATENT DOCUMENTS

| | | | |
|---|---|---|---|
| 6,263,248 B1 | 7/2001 | Farley et al. | |
| 6,638,273 B1 | 10/2003 | Farley et al. | |
| 6,773,428 B2 | 8/2004 | Zappala | |
| 7,967,782 B2 | 6/2011 | Laufer et al. | |
| 7,976,536 B2 | 7/2011 | Farley et al. | |
| 8,007,458 B2 | 8/2011 | Lennox et al. | |
| 9,044,209 B2 | 6/2015 | Dayton et al. | |
| 2006/0129028 A1* | 6/2006 | Krakousky | A61N 1/36007 600/38 |
| 2007/0276342 A1 | 11/2007 | Lin et al. | |
| 2009/0048537 A1 | 2/2009 | Lydon et al. | |
| 2011/0077458 A1* | 3/2011 | Rezai | A61N 1/36107 600/40 |
| 2015/0335431 A1* | 11/2015 | Gettman | A61B 90/37 600/40 |
| 2018/0098855 A1* | 4/2018 | Crabb | A61F 2/26 |
| 2019/0350712 A1* | 11/2019 | Weber | A61F 2/26 |
| 2021/0236288 A1* | 8/2021 | Hamlin | A61F 2/26 |

FOREIGN PATENT DOCUMENTS

| | | |
|---|---|---|
| CN | 101400384 A | 4/2009 |
| RU | 2438595 C1 | 1/2012 |
| SU | 1179973 A1 | 9/1985 |

* cited by examiner

*Primary Examiner* — Samuel G Gilbert
(74) *Attorney, Agent, or Firm* — John Rizvi; John Rizvi, P.A—The Patent Professor®

(57) ABSTRACT

The present invention is directed to a method of penile prosthesis implantation that is minimally invasive, particularly in comparison to traditional methods of penile prosthesis implantation. The implantation method utilizes image guidance and a catheter deployment system for implanting a penile prosthesis into the corporal body of a penis of a patient. More specifically, the implantation method may utilize the Seldinger technique and/or a modified Seldinger technique for implanting the prothesis. The method of implantation may result in more accurate placement, better cosmetic results, faster healing, and less likelihood for infections and other complications.

22 Claims, 7 Drawing Sheets

PENILE PROSTHESIS IMPLANTATION SYSTEM

CROSS-REFERENCE TO RELATED APPLICATIONS

This application claims the benefit of U.S. Provisional Patent Application No. 63/152,123, filed on Feb. 22, 2021, which is incorporated by reference herein in its entirety.

FIELD OF THE INVENTION

The present invention relates generally to the field of implantable devices. More particularly, the present invention relates to a method of penile implant placement. Penile prosthesis implantation is a type of surgery performed on patients with refractory erectile dysfunction and for whom drugs are often not an option. Such surgeries are invasive and may involve possible complications. The disclosed invention aims to provide a less invasive and improved no touch technique procedure for penile prosthesis implantation.

BACKGROUND OF THE INVENTION

Broadly defined, erectile dysfunction (ED) refers to the inability to get or keep an erection firm enough to engage in sexual intercourse. ED typically becomes more common as men age. In the United States it is estimated that at least 12 million men between the ages of 40 and 79 have ED.

ED has a number of vascular, neurological, physiological, and hormonal causes. Conditions commonly associated with ED include: diabetes, hypertension, high cholesterol, obesity, testosterone deficiency, physical trauma, and prostate cancer treatment. Additionally, many medications are known to either cause or exacerbate ED, such as various antidepressants. In particular, selective serotonin inhibitors such as Celexa®, Prozac®, Paxil®, and Zoloft® may cause ED. Tobacco, alcohol, and illicit drugs may also cause ED.

There are a number of potential treatment options for those who have ED. The first common treatment option has to do with lifestyle modifications. Regular exercise, weight loss in obese or overweight men, and improved control of diabetes, hypertension, and high cholesterol are all lifestyles changes that may help patients that have ED. Refraining from tobacco and alcohol use are other highly recommended lifestyle changes that are known to improve the sexual health of those that have ED.

With respect to medications to treat ED, oral PDE-5 inhibitors are typically the first-line treatment. Because sexual stimulation is needed to produce an erection, PDE-5 inhibitors enhance the effects of nitric oxide in the body, which work with other substances to open blood vessels and increase blood flow to the penis. Common medications of this type include Viagra®, Stendra®, Cilais®, and Levitra®.

While medications may work for a number of patients, there are many others for whom such medications are either ineffective or not an option. For instance, those that have experienced some type of trauma to the penis may not benefit from PDE-5 inhibitors. Additionally, there may be a whole class of patients for whom PDE-5 inhibitors do not work because of underlying health conditions. Such health conditions may include issues with nerve, blood vessel, and hormonal dysfunction, where medications would be ineffective at those target sites, or in patients with underlying cardiovascular disease and on medications contraindicated for concomitant use with other vasodilators (i.e. PDE-5 inhibitors). In cases where oral medication is not effective or not an option for those with ED, an increasingly common solution are implantable penile prostheses.

Prosthetic devices have been used to augment, replace, or restore penile function for hundreds of years. Modern prosthetic devices, however, are roughly 50 years old with gradual improvements made over that time. In the United States, it is estimated that approximately 25,000 penile prosthesis procedures occur every year. The primary goal of a penile prosthesis is to restore normal erectile function to allow penetrative sexual activity.

Penile prostheses typically come in two forms-a malleable device and an inflatable device. The simplest type of prosthesis consists of a pair of malleable rods surgically implanted within the erection chambers of the penis. With this type of implant the penis is always semi-rigid and merely needs to be lifted or adjusted into the erect position to initiate sex. A more common type of prosthesis is the inflatable, hydraulic prosthesis. The inflatable penile prosthesis consists of two attached cylinders, a reservoir, and a pump, which are placed surgically in the body. The two cylinders are inserted in the penis and connected by tubing to a separate reservoir of saline. A pump is also connected to the system and sits within the loose skin of the scrotal sac, between the testicles. This system is inflated and deflated on demand by the patient and produces natural looking and rigid erections and is concealable when it is deflated or flaccid.

Device implantation during penile prosthesis procedures does not come without risks, and as the frequency of device implantation increases, so do associated complications. Broadly speaking, complications are associated with such procedures are categorized as infectious, noninfectious tissue-related, device-related, or related to patient and partner satisfaction. With respect to the procedure itself, infectious and noninfectious tissue-related complications are the types of complications that may be mitigated by preoperative, operative, and postoperative care.

Because penile prostheses procedures are invasive in nature, there are risks of infection that arise as a result of the procedure. Infections of the surgical site are to be differentiated from infections of the device itself. Surgical site infections present rapidly after surgery, involve the skin only, and can be treated with antibiotics as any other surgical site infection. Infections related to the device are diagnosed and treated differently than surgical site infections. The majority of postoperative prosthesis infections occur within the first 3 months of device implantation. Acute infections may present similarly to surgical site infections with erythema at the incision but may also have persistent or worsening postoperative pain, an elevated white blood cell count, or tethering of the scrotal pump and tubing to surrounding tissues. Chronic infections or infections occurring after 6 weeks are more commonly subclinical with patients presenting with chronic pain at device components or device extrusion. Typically, these infections are associated with common skin flora due to biofilm formation following bacterial contamination at the time of surgery.

Another complication associated with penile prostheses procedures is the risk of proximal or distal corporal perforation, or urethral perforation in patients who have significant corporal fibrosis, as in cases of diabetes, prior intracavernosal injections, ischemic priapism, Peyronie's disease, or prior prosthesis removal without immediate salvage. Patients who have had infection of the cavernous bodies following an injection program, or those who have experienced priapism, or those who have had trauma to the penis (such as the implantation and removal of the penile prosthesis) will have varying degrees of scar tissue present within the tissue of the corpora cavernosa. Gaining access to fresh spongy tissue at the corporatomy site will usually facilitate dilation proximally and distally more readily than if access is gained through a scarred area. However, even after employing progressive dilation techniques, there remains a risk that the proximal end of the device may perforate, resulting in device placement outside of the corpora cavernosa.

Accordingly, there remains a need in the art for a solution to at least one of the aforementioned problems. For instance, a less invasive procedure that can limit both surgical site infections, as well as infections relating to the placement of the device is desired. Additionally, it is also desired to provide a procedure that can more easily place the device within the corpora cavernosa, particularly in patients with a high risk for corporal perforation, prior perforation and requiring revision, and in patients with fibrosis or high risk of fibrosis. Lastly, a prosthetic device is desired that may increase satisfaction between patient and partner.

SUMMARY OF THE INVENTION

The present invention is directed to a method of penile prosthesis implantation system that is minimally invasive, particularly in comparison to traditional methods of penile prosthesis implantation. The implantation method utilizes image guidance and a catheter deployment system for implanting a penile prothesis into the corporal body of a penis of a patient. More specifically, the implantation method may utilize the Seldinger technique and/or a modified Seldinger technique for implanting the prothesis. Additionally, the prosthesis may be implanted using utilizing a "no touch" technique, such as, for instance, utilizing a pusher for the plurality of steps during the placement.

The implantation method may provide a number of advantages over conventional penile implantation methods. Firstly, because the implantation method utilizes image guidance, the prosthesis may be more accurately placed within the penis and may be used to determine optimal device length. Device malposition may include migration of the reservoir, erosion of the reservoir through the abdominal wall or adjacent organs, and migration of the posterior and anterior portions of the penile prosthesis. Each of these placement issues may negatively impact device function and lead to sexual complications, thus the implantation method disclosed herein looks to avoid or limit these issues. Secondly, the implantation method may lead to less complications during surgery. This is because real-time imaging may reduce damage to critical structures (i.e. blood vessels, urethra, etc.) and produce less trauma. Lastly, the implantation method disclosed herein being minimally invasive in nature, allows for a smaller incision size which in turn may result in better cosmetic results, faster healing, and a lower infection rate. These benefits, in particular less trauma and infection rates, as well as more optimal position of the prosthesis, could help reduce the degree of post-operative scarring and may improve overall erection size, performance, and outcomes.

In a first implementation of the invention, a method of implanting a penile prosthesis into a penis of a patient comprises:
creating at least one incision along a shaft of the penis;
utilizing image guidance to gain needle access to at least one corporal body of the penis; and
employing a catheter delivery system to implant the penile prosthesis within the shaft of the penis; wherein the catheter delivery system includes
utilizing at least one of the Seldinger technique and the accelerated Seldinger technique for implanting the penile prosthesis into the penis.

In a second aspect, the at least one incision may be at the dorsal aspect of the penis.

In another aspect, the at least one incision may be at the ventral aspect of the penis.

In another aspect, the at least one incision may be on the side of the penis.

In another aspect, the at least one incision may be at the proximal aspect of the penis.

In another aspect, the at least one incision may be at the lateral aspect of the penis.

In another aspect, the proximal aspect of the penis may be penscortal.

In another aspect, the at least one incision may at the distal aspect of the penis.

In another aspect, the distal aspect of the penis may be subcoronal.

In another aspect, the imagine guidance utilized may be ultrasound.

In another aspect, ultrasound may be used to determine cross-sectional dimensions of the penis and corporal bodies.

In another aspect, ultrasound may be used to estimate corporal length for penile prosthesis sizing.

In another aspect, the cross-sectional dimensions of the penis determined from ultrasound may be used to create optimal dimensions of the penile prosthesis.

In another aspect, the image guidance utilized may be magnetic resonance imaging (MRI).

In another aspect, the image guidance utilized may be a computerized tomography (CT) scan.

In another aspect, the image guidance utilized may be fluoroscopy.

In another aspect, the image guidance utilized may be some combination of MRI, CT scan, ultrasound, and fluoroscopy.

In another aspect, the catheter delivery system may further include at least one of a plurality of scout needles, thin wires, thick wires, rigid wires, flaccid wires, dilators, catheters, and Peel-Away® catheters and sheaths for implanting the penile prosthesis into the penis.

In another aspect, the catheter delivery system may include a series of progressively larger dilator catheters which can be placed over a wire, and a balloon catheter which can be placed over the wire, wherein the balloon catheter may be expanded to dilate a corporal body implant site of the penis, after which the catheter may be removed and the prosthesis may be placed directly over the wire.

In another aspect, the plurality of scout needles, thin wires, rigid wires, flaccid wires, dilators, catheters, and Peel-Away® catheters and sheaths may be coated.

In another aspect, the catheter delivery system may include markings on the at least one of a plurality scout needles, thin wires, thick wires, rigid wires, flaccid wires, dilators, catheters, and Peel-Away® catheters and sheaths wherein the markings may be visible under image guidance.

In another aspect, the penile prosthesis may be passed over the at least one of the plurality of scout needles, thin wires, thick wires, rigid wires, flaccid wires, dilators, catheters, and Peel-Away® catheters and sheaths.

In another implementation of the invention, a penile prosthesis comprises:

at least one cylindrical rod, the at least one cylindrical rod having a proximal end and a distal end;

a central bore on an exterior surface of the at least one cylindrical rod at at least one of the proximal end and the distal end; and an exterior attachment on the exterior surface of the at least one cylindrical rod; wherein the central bore and the exterior attachment are configured to be placed over a wire during insertion of the prosthesis.

In another aspect, the penile prosthesis may include a retention system.

In another aspect, the retention system may include at least one of a balloon, stent, or spike.

In another aspect, the penile prosthesis may be rigid.

In another aspect, the penile prosthesis may be semi-rigid.

In another aspect, the semi-rigid penile prosthesis may be comprised of a mesh-like structure configured to expand and contract.

In another aspect, the penile prosthesis may be inflatable and may include a pump and reservoir system.

In another aspect, the penile prosthesis may change form, shape, or dimensions from either an internal or an external stimulus.

In another aspect, the stimulus may be an electrical or a temperature change.

In another aspect, the electrical stimulus may be triggered from a battery within the penile prosthesis.

In another aspect, the penile prosthesis may include biometric and smart device inputs and outputs.

In another aspect, the biometric and smart device inputs may be for instance, pulse, breathing, and tactile sensation wherein the output may be the penile prosthesis expanding or getting larger, resulting in an erection.

In another aspect, the biometric and smart device inputs may be the sound of a voice or the sound of particular music.

In another implementation of the invention, a penile prosthesis implantation system comprises:

a prosthesis comprising at least one cylindrical rod, the at least one cylindrical rod having an at least one of a central bore and an exterior attachment, the central bore and the exterior attachment configured to be placed over a wire during an implantation of the prosthesis; where implantation of the prosthesis includes:

creating at least one incision along a shaft of a penis;

utilizing image guidance to gain needle access to at least one corporal body of the penis; and employing a catheter delivery system to implant the penile prosthesis within the shaft of the penis; wherein the catheter delivery system includes utilizing at least one of the Seldinger technique and the accelerated Seldinger technique for implanting the penile prosthesis into the penis.

These and other objects, features, and advantages of the present invention will become more readily apparent from the attached drawings and the detailed description of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper", "lower", "left", "rear", "right", "front", "vertical", "horizontal", and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Shown throughout the figures, the present invention is directed toward a penile prosthesis implantation system that is designed to provide a less invasive alternative for implantation compared to conventional methods. The method provided may utilize image guidance, as well as a catheter delivery system to implant a penile prosthesis in the penis of a patient with refractory erectile dysfunction (ED). Penis may refer to the patient's native penis, a transplanted penis, a reconstructed penis in someone with gender reassignment surgery, or a reconstructed or grafted penis following severe trauma. The use of image guidance in the method of implantation may allow for the prosthesis to be more accurately placed, may result in fewer complications compared to more invasive procedures, and may also allow for direct measurements to increase accuracy in optimal sizing of the implant.

Figure 2:
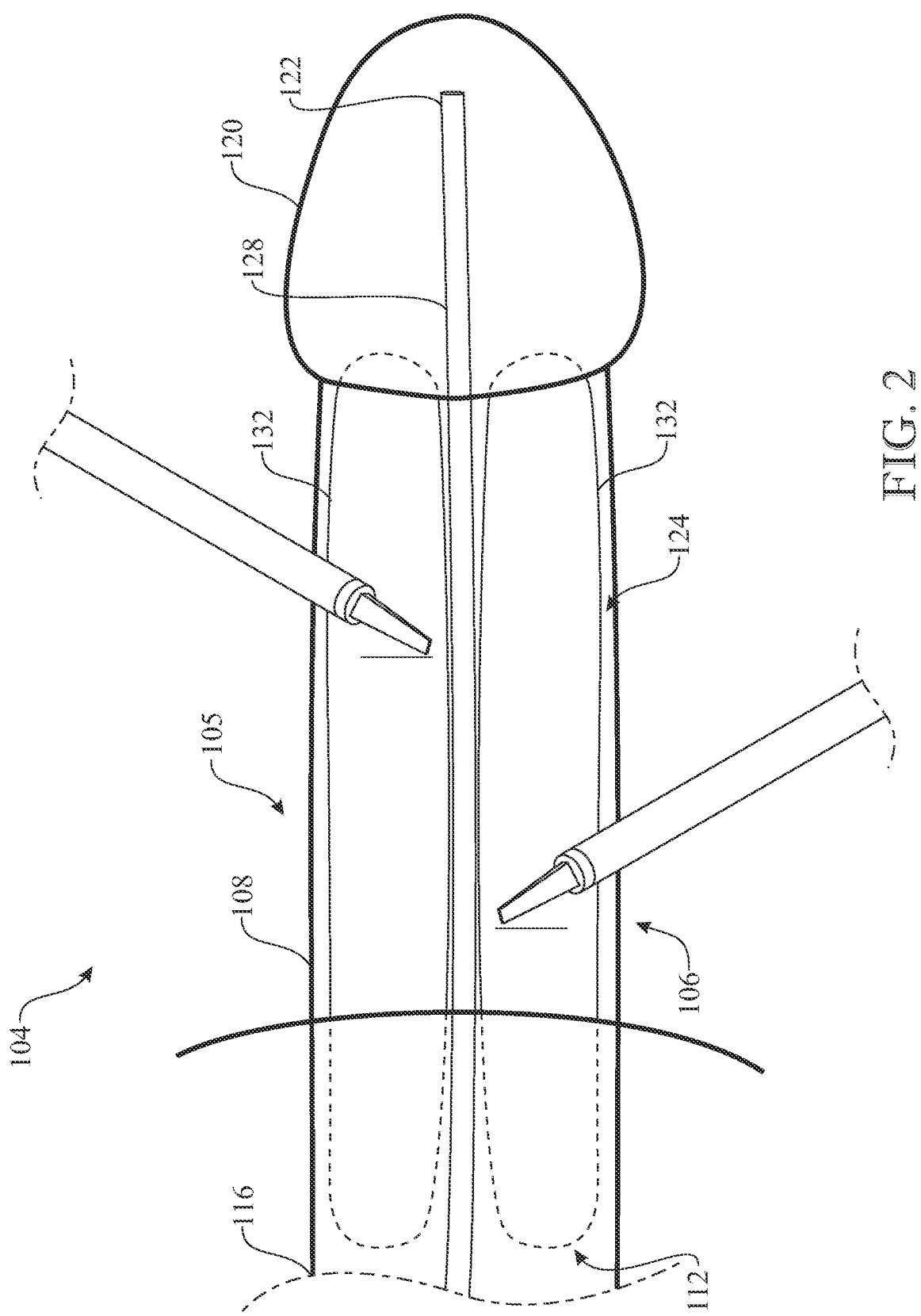
FIG. 2 presents a top horizontal view of a penis prior to an incision being created.

Referring initially to FIG. 2, for reasons that will be apparent hereinafter, various parts of the male anatomy are described herein such that a method of implanting a penile prosthesis 100 may be more comprehensively described in this description. The method of implanting a penile prosthesis 100 includes implanting a prosthesis into a penis 104 of a patient. The penis 104 is an organ that may include an external surface 108 and an internal body 112. The penis 104 may further include a proximal end having a base 116 and a distal end having a glans penis (tip) 120. The penis 104 may also be roughly cylindrical in shape and may include a dorsal aspect 105 and a ventral aspect 106. The area of the penis 104 connecting the base 116 to the tip 120 may be referred to as the shaft 124. The external surface 108 of the shaft 124 of the penis may be comprised of skin and may be include foreskin covering the tip 120 of the penis 104. The tip 120 may include a meatus 122 which may be an opening designed to release urine and semen from the penis 104.

Figure 4:
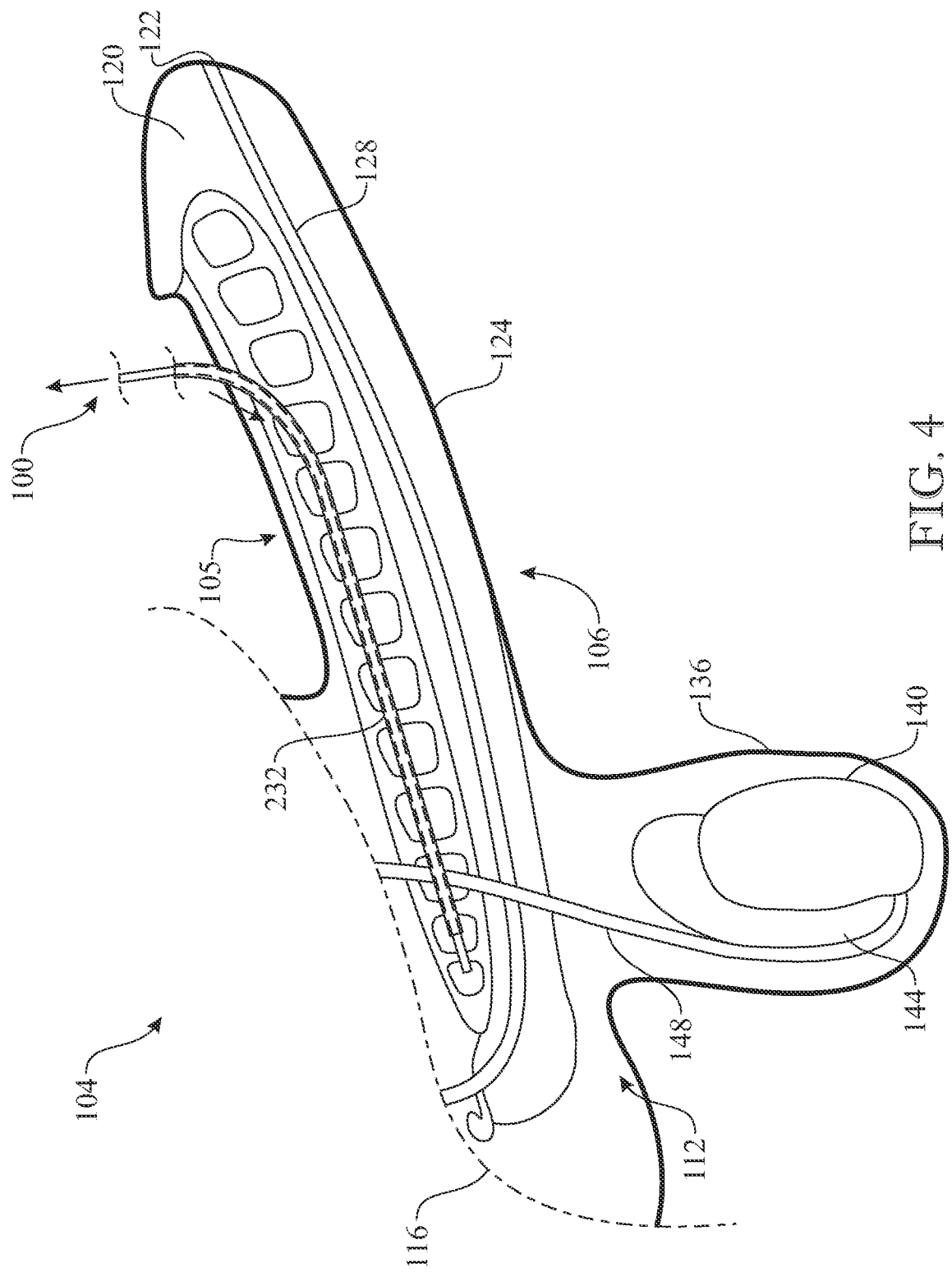
FIG. 4 presents an internal side view of the penis after insertion of a catheter over the wire within the corporal body of the penis.

As best shown in FIG. 4, the internal body 112 of the penis 104 may be comprised of a number of different anatomical parts. From the base 116 of the penis 104 through the tip 120 of the penis may be a urethra 128. The urethra 128 may be duct designed for carrying, holding, and releasing urine and semen through the meatus 122. Within the internal body 112 of the shaft 124 of the penis 104 may be three columns of tissue. There may be two corpus cavernosa 132 on the dorsal side 105 of the penis 104 and a corpus spongiosum (not shown) on the ventral side 106 of the penis 104, surrounding the urethra 128. Hanging from the shaft 124 of the penis 104 may be a scrotum 136. Within the scrotum 136 may be at least one testicle 140. The at least one testicle 140 may be where sperm is produced. Attached to the at least one testicle may be an epididymis 144. The epididymis 144 may be a duct wherein the sperm is stored before travelling through a vas deferens duct 148 which transports the sperm to the urethra 128.

Figure 1:
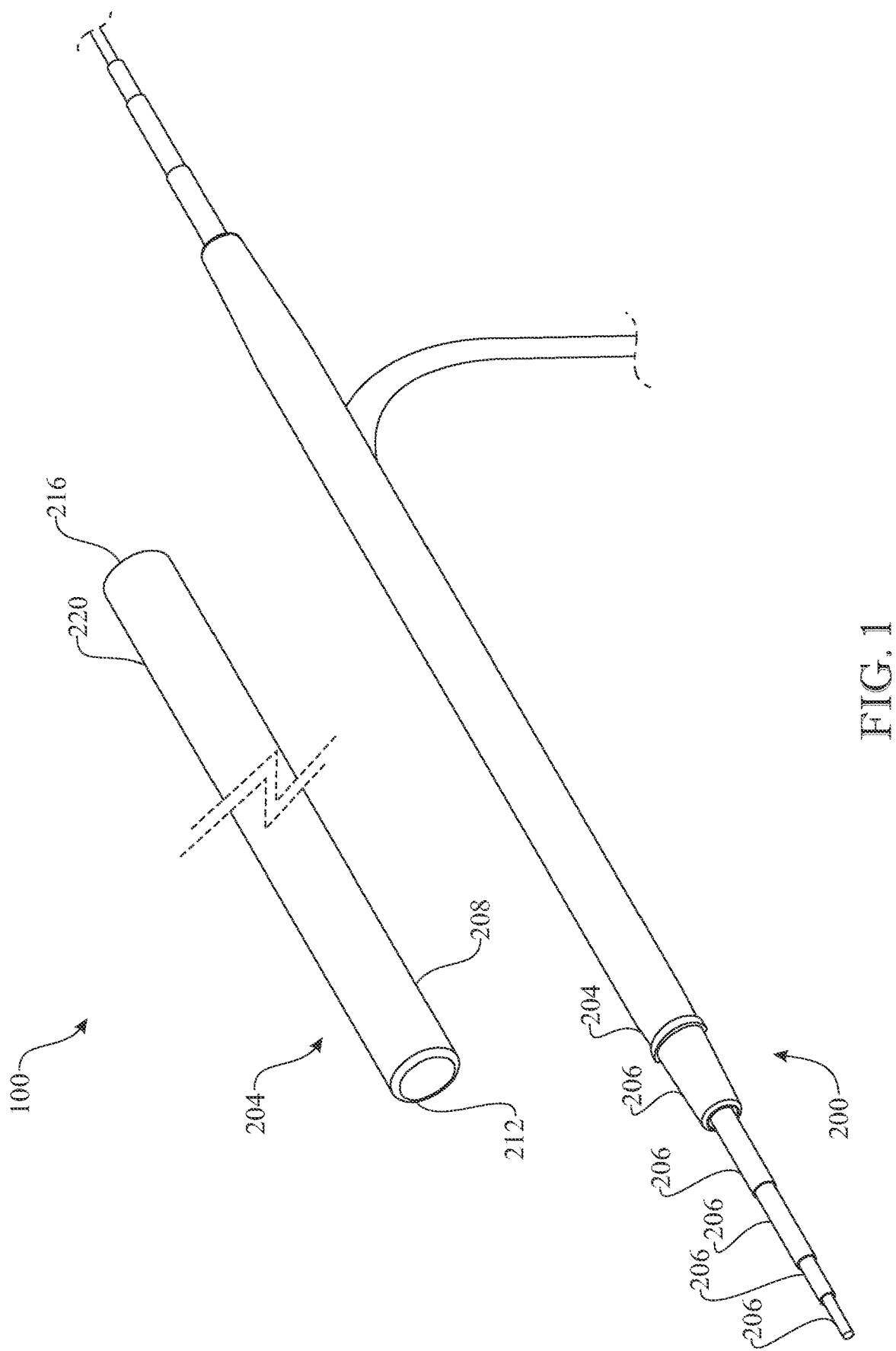
FIG. 1 presents a front isometric view of the catheter delivery system of the penile implantation method in accordance with a first illustrative embodiment of the invention.

Referring now to FIG. 1, the method of implanting a penile prosthesis 100 is shown in conjunction with a catheter delivery system 200. The catheter delivery system 200 may include a series of needles, wires, dilators, and catheters to implant the penile prosthesis 204. The catheter delivery system 200 may utilize the Seldinger method or the accelerated Seldinger method for implanting the prosthesis 204 utilizing at least one of a plurality of scout needles, thin wires, rigid wires, flaccid wires, dilators, and catheters 206. The plurality of scout needles, thin wires, rigid wires, flaccid wires, dilators, and catheters 206 may be coated with a material allowing for each to more easily slide over one another during the implantation procedure. This feature may allow for pushing the prosthesis 204 in place over the wire 206 so as to minimize touching the prosthesis 204 and in turn, minimize the risk of infection. Additionally, the catheter delivery system 200 may include markings on the at least one of a plurality scout needles, thin wires, thick wires, rigid wires, flaccid wires, dilators, and catheters 206 wherein the markings may be visible under image guidance. This feature may allow for better visualization during the implantation and can allow for direct measurements to be made. For instance, the wire may be placed at the tip 120 and the base 116 of the penis 104 and the sum length from a distal aspect of the penis to an at least one incision site may be the desired length of the prosthesis 204.

With continued reference to FIG. 1, the penile prosthesis 204 may be a cylindrical rod 208 having a proximal end 212 and a distal end 216. The cylindrical rod 208 may additionally include an exterior surface 220 and a hollow interior surface (not shown). The hollow interior surface may define an interior space (not shown). The cylindrical rod 208 may be rigid or semi-rigid. Additionally, the prosthesis 204 may be malleable. The malleability of the prosthesis 204 may allow for position memory such that a patient may manually adjust the rod 208 after insertion by contorting their penis 104. Alternatively, embodiments are envisioned where the prosthesis 108 may be inflatable and may include a pump and a reservoir in the scrotum 136 for pumping a solution into the interior space of the prosthesis 204. The prosthesis 204 may be made of a spiral wire core a silicone material, wrapped in either silicone or polyurethane. The prosthesis may also be made of Bioflex®. Additionally, the penile prosthesis 204 may include a retention device to hold the prosthesis 204 in place within the penis 104. Such a retention device may be, for instance, a balloon, a stent, a spike, or other deployable retention system. Additionally, the penile prosthesis 204 may be able to change for, shape, or dimensions as a result of internal or external stimuli. More specifically, the penile prosthesis 204 may include biometric and smart device input and outputs such a user's pulse, breathing, and tactile sensation wherein the output may be the penile prosthesis 204 expanding or getting larger, resulting in an erection for the user.

The method of implantation of the penile prosthesis 108 may begin by adequately preparing the patient. This may include draping the patient in a surgical gown and administering general anesthesia as is common in surgical procedures. The patient may be placed supine on an operating table with their pelvis uncovered. As best shown in FIG. 2, a surgeon may then stretch the penis 104 of the patient such that the penis 104 is at an erect length and held in place. The surgeon may then use image guidance to determine both the erect length of the patient's penis 104, as well as any vascular or anatomic abnormalities in the penis 104. Additionally, image guidance may be used to determine the length and diameter of the each of the corpus cavernosa 132, wherein the prosthesis 104 may be inserted. By determining the length of the penis 104, an appropriately sized prosthesis 104 may be selected by the surgeon. In some embodiments, such as the present embodiment, the image guidance used may be ultrasound. Alternatively, the image guidance used the may be magnetic resonance imaging (MRI). Embodiments are envisioned wherein the image guidance may be a computerized topography (CT) scan or fluoroscopy or some combination of ultrasound, MRI, CT scan, and fluoroscopy.

With continued reference to FIG. 2, upon determining the size of the penis 104 and the appropriate size of prosthesis 204 to use, the surgeon may then create the at least one incision 224 at the ventral aspect 106 of the base 116 of the penis 104. In the preferred embodiment, the surgeon may make two incisions 224, one into each corpus cavernosa 132. Embodiments are also envisioned in which the incisions 224 are made at the distal end of the penis 104 at the end of the shaft 124 prior to the tip 120, as shown in FIG. 4. Additionally, embodiments are envisioned wherein the at least one incision 224 is made at the dorsal aspect 105 of the penis 104, or the side of the penis 104. The at least one incisions 224 may be approximately 2 mm in size.

Figure 3:
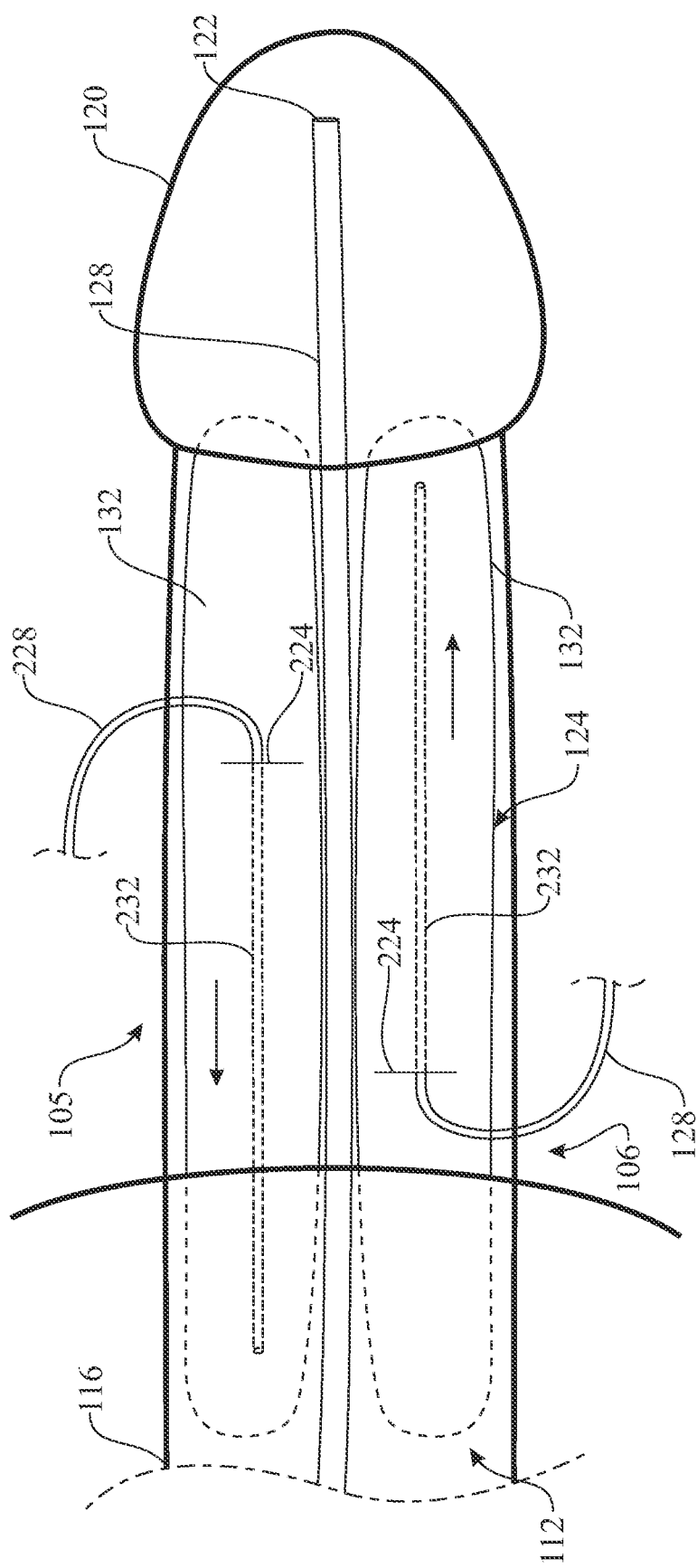
FIG. 3 presents a top view of the penis after an incision has been made and after a wire has been inserted into the corporal bodies of the penis.
Figure 5:
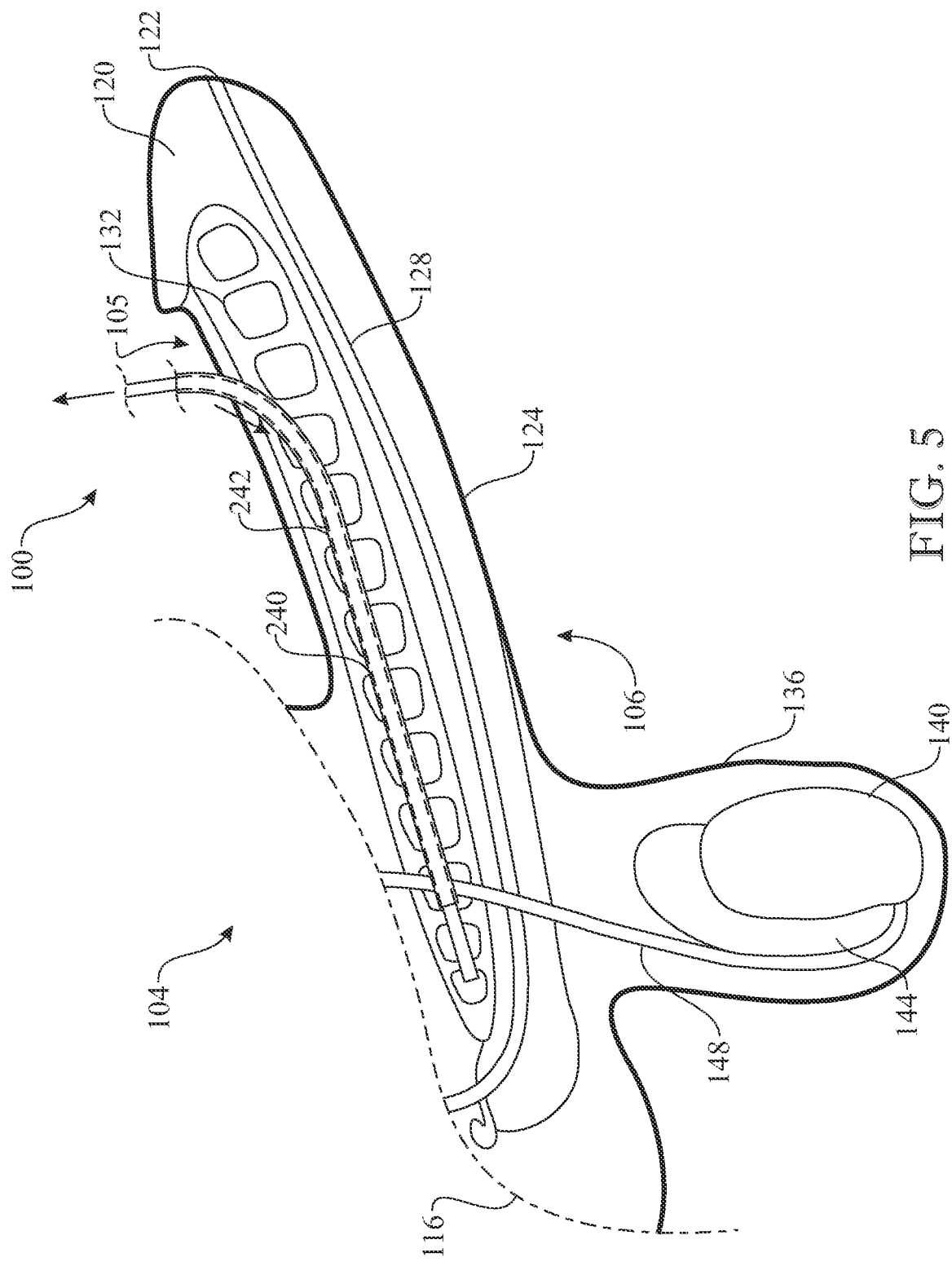
FIG. 5 presents an internal side view of the penis after insertion of a thicker wire and a thicker catheter than the wire and catheter found in FIG. 4.
Figure 6:
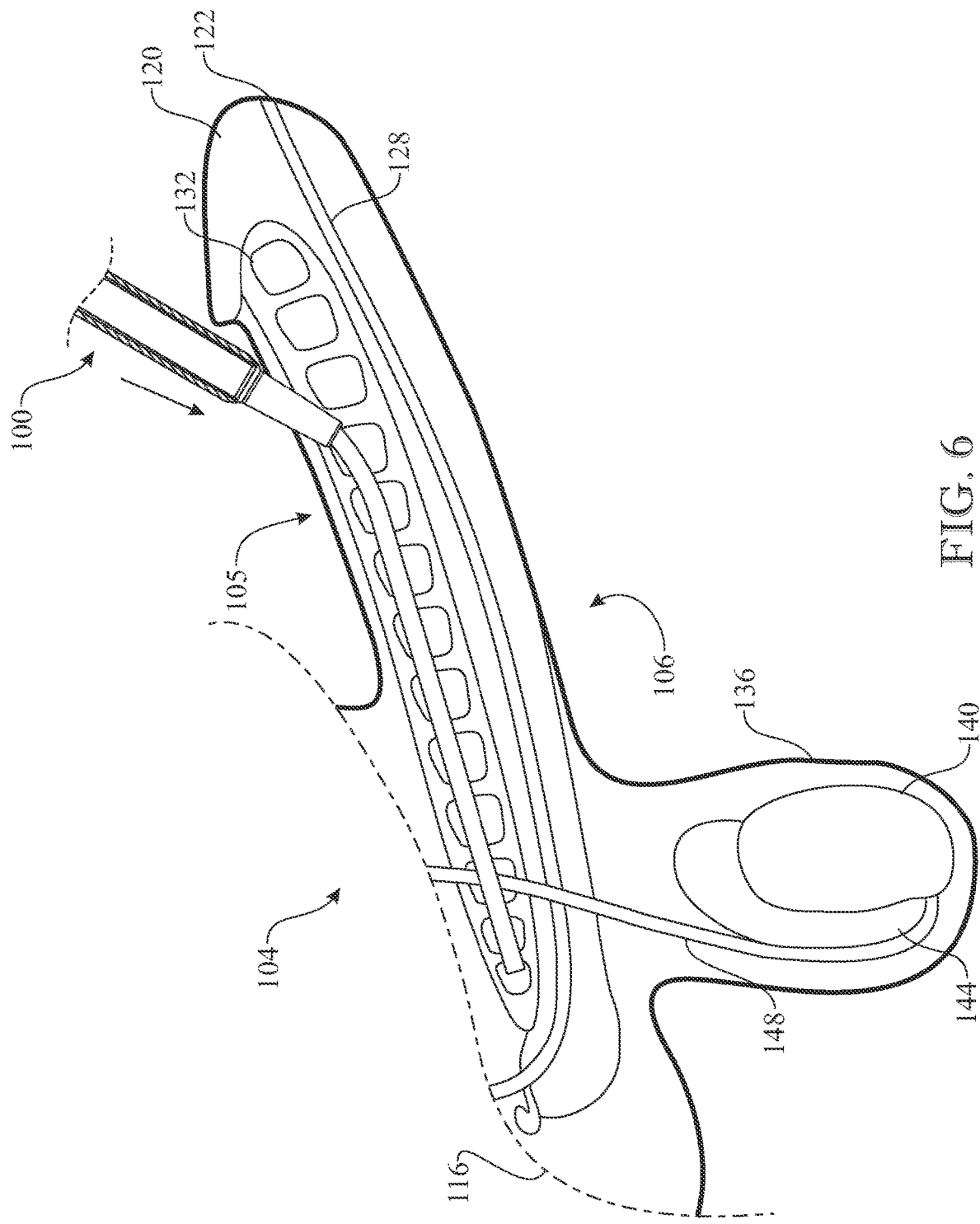
FIG. 6 presents an internal side view of the penis after insertion of a thicker wire and a thicker catheter than the wire and catheter found in FIG. 5.
Figure 7:
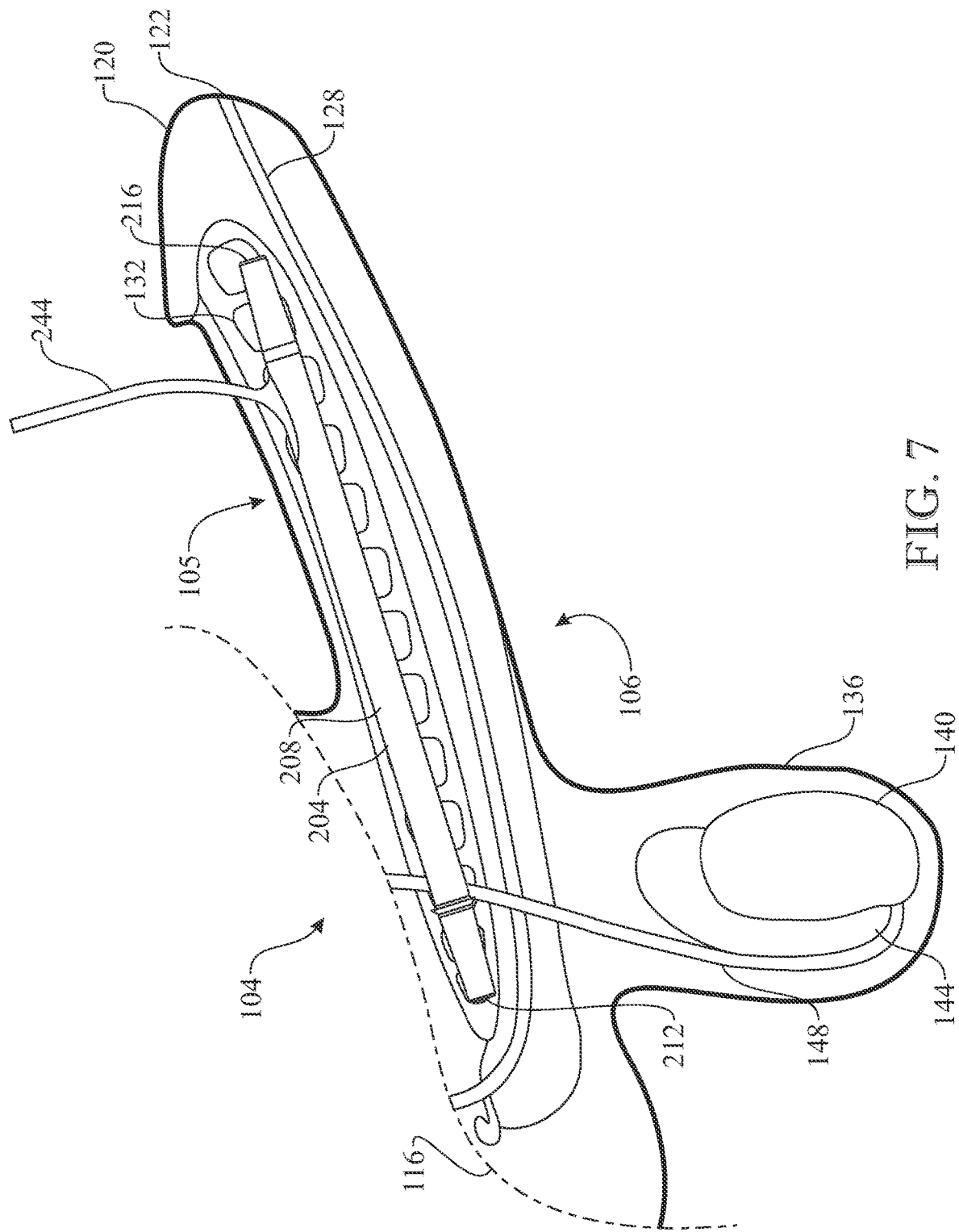
FIG. 7 presents an internal side view of the penis after insertion of the penile prosthesis within the corporal body of the penis.

Referring now to FIG. 3, a needle 228 may be placed through the at least one incision 224 into a corpus cavernosa 132 of the penis 104 using image guidance. Continuing to use imaging guidance, the surgeon may then place a small wire 232 through the needle 228 and towards the base 116 of the penis 104. The needle 228 may then be withdrawn and a dilator/catheter 236 is placed over the small wire 232, as best shown in FIG. 4. The small wire 232 may then be withdrawn and a thicker wire 240 may be placed through the dilator/catheter 236, as shown in FIG. 5. The dilator/catheter 236 may then be withdrawn and a thicker dilator/catheter 242 may be placed over the wire 240. Serial wire and catheter exchanges may be made until the desired cavity size is made in the corpus cavernosa 132, as shown in FIG. 6. Over the last placed wire may be the prosthesis 204. All such exchanges are completed using imaging guidance and may conform with the Seldinger technique to reach the desired cavity size within the corpus cavernosa 132. A new needle may then be placed next to the prosthesis 204. Then a wire 244 may be placed in the direction of the tip 120 of the penis 104. The distal end 216 of the prosthesis 204 may then be passed over the wire 244 and into the corpus cavernosa 132 in the direction of the tip 120 of the penis 104. The wire 244 may then exit through an opening along the cylindrical rod 208 of the prosthesis 204 such that prosthesis 204 is held in place within the penis 104, as shown in FIG. 7. Each of these steps may be repeated for the adjacent corpus cavernosa 132, such that at least two cylindrical rods 208 may be placed within the penis 104. The surgeon may then suture or repair the corpus cavernosa 132 and any underlying tissue surrounding the corpus cavernosa 132. The procedure may be completed by closing each of the at least one incision 224 on the external surface 108 of the penis 104.

Alternative embodiments are contemplated to those shown or described herein without departing from the scope of the present disclosure. For example, embodiments are contemplated in which the type of prosthesis being implanted varies. In the embodiment shown, a rigid or semi-rigid prosthesis is used. However, embodiments are envisioned in which the method of implantation may be used with an inflatable prosthesis such that a pump and reservoir may also be inserted. Another alternative embodiment considered is applying the method to prostheses having varying retention methods, such as, but not limited to: retention rod systems, memory material systems, self-expanding systems, and electrical or heat shape shifting systems.

In summary, the implantation method disclosed herein provides a more accurate and less invasive method for implanting penile prostheses. In particular, the use of imaging guidance and the less invasive nature of the method also may help in limiting complications and infections. Lastly, the method disclosed may result in better cosmetic results and faster healing.

Since many modifications, variations, and changes in detail can be made to the described preferred embodiments of the invention, it is intended that all matters in the foregoing description and shown in the accompanying drawings be interpreted as illustrative and not in a limiting sense. Furthermore, it is understood that any of the features presented in the embodiments may be integrated into any of the other embodiments unless explicitly stated otherwise. The scope of the invention should be determined by the appended claims and their legal equivalents.

What is claimed is:

1. A penile prosthesis implantation kit comprising:
   a prosthesis comprising at least one elongate member, the at least one elongate member being configured to be placed over a wire and through a catheter during an implantation of the prosthesis;
   a wire adapted to be placed in the penis and configured for placing the penile implant over the wire for implantation; and
   a catheter delivery system used over the wire for dilating an opening in the penis and to implant the penile prosthesis into the opening in the penis by delivering the penile implant through the catheter.

2. The penile prosthesis implantation kit of claim 1, wherein the penile prosthesis includes any foreign body implanted into the penis.

3. The penile prosthesis implantation kit of claim 1, wherein the penile prosthesis includes a central bore and an exterior attachment.

4. The penile prosthesis implantation kit of claim 1, wherein the penile prosthesis includes a retention system.

5. The penile prosthesis implantation kit of claim 4, wherein the retention system includes at least one of a balloon, stent, or spike.

6. The penile prosthesis implantation kit of claim 1, wherein the penile prosthesis is at least one of rigid and semi-rigid.

7. The penile prosthesis implantation kit of claim 6, wherein the semi-rigid penile prosthesis is comprised of a mesh-like structure configured to expand and contract.

8. The penile prosthesis implantation kit of claim 1, wherein the penile prosthesis is inflatable and includes a pump and reservoir system.

9. The penile prosthesis implantation kit of claim 1, wherein the penile prosthesis is configured to change form, shape, or dimensions from either an internal or an external stimulus.

10. The penile prosthesis implantation kit of claim 9, the stimulus is at least one of an electrical and a temperature change.

11. The penile prosthesis implantation kit of claim 10, wherein the electrical stimulus is triggered from a battery within the penile prosthesis.

12. The penile prosthesis implantation kit of claim 1, wherein the penile prosthesis includes biometric and smart device inputs and outputs.

13. The penile prosthesis implantation kit of claim 12, wherein the biometric and smart device inputs include pulse, breathing, and tactile sensation and further wherein the output includes the penile prosthesis expanding or getting larger.

14. The penile prosthesis implantation kit of claim 13, wherein the biometric and smart device inputs include at least of the sound of a voice and the sound of particular music.

15. The penile prosthesis implantation kit of claim 1, wherein the kit further comprises an image guidance system adapted to determine cross-sectional dimensions of the penis and to place the penile implant through the catheter, wherein the image guidance system is least one of ultrasound, magnetic resonance imagining (MRI), computerized tomography (CT) scan, and fluoroscopy.

16. The penile prosthesis implantation kit of claim 15, wherein only ultrasound is used to determine cross-sectional dimensions of the penis, and further wherein the cross-sectional dimensions of the penis determined from ultrasound may be used to create optimal dimensions of the penile prosthesis.

17. The penile prosthesis implantation kit of claim 15, wherein ultrasound is used to determine a corporal length, and further wherein the corporal determined from ultrasound may be used to create optimal sizing of the penile prosthesis.

18. The penile prosthesis implantation kit of claim 1, wherein the catheter delivery system may further include at least one of a plurality of scout needles, thin wires, thick wires, rigid wires, flaccid wires, dilators, catheters, and sheaths for implanting the penile prosthesis into the penis.

19. The penile prosthesis implantation kit of claim 18, wherein the catheter delivery system includes a series of progressively larger dilator catheters configured to be placed over a wire, and a balloon catheter also configured to be placed over the wire, wherein the balloon catheter is expanded to dilate a corporal body implant site of the penis, after which the catheter is removed and the prosthesis is placed directly over the wire.

20. The penile prosthesis implantation kit of claim 18, wherein the catheter delivery system includes markings on the at least one of a plurality scout needles, thin wires, thick wires, rigid wires, flaccid wires, dilators, catheters, and sheaths, and further wherein the markings may be visible under image guidance.

21. A penile prosthesis implantation kit configured to insert a prosthesis into a penis of a patient comprising:
    a prosthesis comprising at least one elongate member, the at least one elongate member having an at least one of a central bore and an exterior attachment, the central bore and the exterior attachment configured to be placed over a wire during an implantation of the prosthesis, the penile prosthesis being configured to change form, shape, or dimensions from either an internal or an external stimulus;
    a wire adapted to be placed in the penis and configured for placing the penile implant over the wire for implantation;
    a catheter delivery system used over the wire for dilating an opening in the penis and to implant the penile prosthesis into the opening in the penis by delivering the penile implant through the catheter; and
    an image guidance system adapted to determine cross-sectional dimensions of the penis and to place the penile implant through the catheter, wherein the image guidance system is least one of ultrasound, magnetic resonance imagining (MRI), computerized tomography (CT) scan, and fluoroscopy.

22. A penile prosthesis implantation system kit to insert a prosthesis into a penis of a patient comprising:
    a prosthesis comprising at least one cylindrical rod, the at least one cylindrical rod having an at least one of a central bore and an exterior attachment, the central bore and the exterior attachment configured to be placed over a wire during an implantation of the prosthesis, the penile prosthesis being configured to change form, shape, or dimensions from either an internal or an external stimulus;
    a wire adapted to be placed in the penis and configured for placing the penile implant over the wire for implantation; and
    a catheter delivery system used over the wire for dilating an opening in the penis and to implant the penile prosthesis into the opening in the penis by delivering the penile implant through the catheter; and
    an image guidance system adapted to determine cross-sectional dimensions of the penis and to place the penile implant through the catheter, wherein the image guidance system is ultrasound.

* * * * *